United States Patent

Maurer et al.

[11] Patent Number: 5,316,784
[45] Date of Patent: May 31, 1994

[54] PROCESS FOR THE PRODUCTION OF A SOLID PHASE MATRIX COATED WITH AN IMMUNOLOGICALLY ACTIVE SUBSTANCE

[75] Inventors: Eberhard Maurer, Weilheim; Rolf Deeg, Bernried, both of Fed. Rep. of Germany

[73] Assignee: Boehringer Mannheim GmbH, Mannheim, Fed. Rep. of Germany

[21] Appl. No.: 994,487

[22] Filed: Dec. 21, 1992

Related U.S. Application Data

[63] Continuation of Ser. No. 545,175, Jun. 28, 1990, abandoned.

[30] Foreign Application Priority Data

Jul. 14, 1989 [DE] Fed. Rep. of Germany ..... 39233421

[51] Int. Cl.$^5$ .................. B05D 3/06; G01N 33/53; G01N 33/543
[52] U.S. Cl. .................. 427/2; 427/508; 427/512; 435/7.92; 436/500; 436/518; 436/532
[58] Field of Search ............... 427/2, 508, 512; 436/532, 518, 500; 435/7.92

[56] References Cited

U.S. PATENT DOCUMENTS

| | | | |
|---|---|---|---|
| 3,888,833 | 6/1975 | Lednicer et al. | 427/2 |
| 4,539,061 | 9/1985 | Sagiv | 427/496 |
| 4,562,157 | 12/1985 | Lowe et al. | 435/291 |
| 4,597,999 | 7/1986 | Lingwood | 427/54.1 |
| 4,689,310 | 8/1987 | Kramer et al. | 436/512 |
| 4,716,122 | 12/1987 | Scheefers | 436/532 |
| 4,737,544 | 4/1988 | McCain et al. | 427/2 |
| 4,784,804 | 11/1988 | Basch et al. | 260/349 |
| 4,810,638 | 3/1989 | Albarella et al. | 435/7 |
| 4,889,816 | 12/1989 | Davis et al. | 436/532 |
| 4,987,032 | 1/1991 | Miyasake et al. | 427/54.1 |
| 5,128,170 | 7/1992 | Matsuda et al. | 427/2 |
| 5,164,299 | 11/1992 | Lambert | 435/7.92 |
| 5,168,057 | 12/1992 | Oh et al. | 435/7.92 |
| 5,217,743 | 6/1993 | Farah | 427/2 |
| 5,240,747 | 8/1993 | Matsuda et al. | 427/2 |
| 5,258,041 | 11/1993 | Guire et al. | 427/2 |

FOREIGN PATENT DOCUMENTS

| | | |
|---|---|---|
| 175973 | 4/1986 | European Pat. Off. |
| 319953 | 6/1989 | European Pat. Off. |
| 410323 | 1/1991 | European Pat. Off. |
| 2533701 | 2/1976 | Fed. Rep. of Germany |
| 8901160 | 2/1989 | PCT Int'l Appl. |

Primary Examiner—Shrive Beck
Assistant Examiner—Diana Dudash
Attorney, Agent, or Firm—Nikaido, Marmelstein, Murray & Oram

[57] ABSTRACT

To produce a solid phase coated with an immunologically active substance, a carrier material is absorptively coated with a mixture of an immunologically active substance and a compound which contains at least two functional groups which can be photoactivated and at least one moiety which interacts with the carrier material and the immunologically active substance and it is subsequently irradiated for the cross-linkage.

13 Claims, 3 Drawing Sheets

PROCESS FOR THE PRODUCTION OF A SOLID PHASE MATRIX COATED WITH AN IMMUNOLOGICALLY ACTIVE SUBSTANCE

This application is a continuation of application Ser. No. 07/545,175 filed Jun. 28, 1990, now abandoned.

The invention concerns a process for the production of a solid phase matrix coated with an immunologically active substance.

In diagnostics, solid phases to which a substance is bound which can bind to the substance to be determined or to a complex of the substance to be determined and a labelled substance are used for many determinations which proceed according to the principle of the heterogeneous immunoassay. In this process, the binding of this specifically bindable material to a solid phase is a major problem. The binding can be adsorptive or covalent, depending on the type of the carrier material. As a rule, a covalent binding requires carrier materials which have corresponding functional groups and immunologically active substances which likewise have corresponding functional groups. These processes are technically very complicated and often influence the activity of the immunologically active substances. Adsorptive binding, which as a rule is better for preserving the activity, has the disadvantage that only an inadequate adhesion to plastic surfaces can be achieved. As a consequence, desorption effects and displacement by serum components or detergents occur during the incubation, which is necessary for carrying out the method of determination, and as a result of influences of temperature and washing. A major disadvantage of the purely adsorptive binding of proteins to plastic surfaces, which is often used, is the inadequate adhesion which causes many problems. Thus, antibodies attached to the tube wall which become detached from the wall can react with the analyte in the test solution and thereby trap the latter which results in false recoveries. In addition, serum components which bind strongly can displace antibodies attached to the tube wall which also leads to false recoveries. A test procedure at a higher temperature, which is aimed for because of the shorter reaction times, is often not possible because of increasingly strong desorption and because of a decrease in signal and recoveries dependent on temperature. Intensive washing steps, which should be carried out to prevent carry-over and, to a greater or lesser degree, to remove non-specifically bound serum components, lead to a considerable detachment of antibodies from the wall which falsifies the recovery and reduces the precision. Also the detergents, which are often used to avoid unspecific binding, interfere with the adsorptive binding and thus lead to a considerable detachment from the wall. As a result of fluctuations in the adsorptive binding properties of the carrier material, which are dependent on the batch, different rates of detachment are obtained which in turn reduces the precision and results in false recoveries. The precision and sensitivity of immunological methods of determination are impaired by all of these problems.

In order to improve the binding of the immunologically active substance to the solid phase, it was suggested in U.S. Pat. No. 4,689,310 that a compound, which has a group which can be photoactivated, be attached covalently either to the carrier material or to the ligand to be bound. When the carrier material and ligand, one of which is correspondingly derivatized, are brought into contact and irradiated a binding between both of them can thus occur. This process is, however, complicated and also does not yield satisfactory results.

It was thus the object of the present invention to provide a process which can be easily carried out and which leads to a very durable binding of an immunologically active substance to the carrier material.

This object is achieved by a process for the production of a solid phase matrix coated with an immunologically active substance, which is characterized in that a carrier material is coated adsorptively with a mixture of
  (a) an immunologically active substance
  (b) a compound which contains at least two functional groups which can be photoactivated and at least one moiety which interacts adsorptively with the carrier material and with the immunologically active substance, and is subsequently irradiated for the cross-linkage.

According to the present invention solid phase matrices can be coated in a simple manner with immunologically bindable substances which remain stable over a long time period and under the influence of temperature and detergents.

The carrier material to be coated is brought into contact with a coating solution which contains the immunologically active substance and the compound containing the groups which can be photoactivated. After a sufficiently long contact time in which light at a wavelength which leads to an activation of the groups which can be photoactivated must be excluded, a surface layer which is at first adsorptively bound forms as a result of the hydrophobic moiety by interaction between protein, the bifunctional compound and the carrier material. After completion of this first incubation it is irradiated with light of a suitable wavelength and intensity. By this means, highly reactive groups such as e.g. carbenes and/or nitrenes are generated on component (b) which react in a rapid and unspecific reaction with the protein as well as with the carrier material in which covalent bonds are formed. The surface layer which is at first adsorptively preformed is fixed covalently in this manner by protein-protein and protein-wall bonds. The efficiency of the coating process and the probability of cross-linkage is considerably increased by the combination of these measures. Furthermore, the immunologically active substance used is optimally utilized by the adsorptive accumulation of protein at the surface and a high coating density is achieved.

The solid phase matrices produced according to the present invention are used for carrying out heterogeneous immunoassays. For this, an immunologically active substance is immobilized on the solid phase. Immunologically active substance is understood here as compounds which can enter into a specific binding with other substances. Antibodies, binding proteins, lectins, biotin, avidin or streptavidin, hormones and other biologically active substances can be named as examples. In particular, immunologically active substances which are capable of binding with the substance to be determined or a complex of substance to be determined and labelled conjugate which is bound to it, come into consideration for use in immunoassays. Thus, antibodies and binding proteins as well as streptavidin or avidin or biotin conjugates are preferably used. Equally suitable are biologically active molecules such as T4, T3 also as a polyhapten, prolactin, LH or TSH as well as antibodies which are directed against them.

The usual materials can be used as carrier material. All materials which react with a group which can be photoactivated with formation of a covalent bond are suitable such as polysaccharides, glass, ceramics, cellulose and plastics for example. By use of the compounds which can be photoactivated, plastics which already have functional groups as well as preferably inert materials such as e.g. polyethylene can be used. In particular, all types of plastics such as e.g. polyamides, polyacrylamides, polyester, polyethylene, polypropylene, silicons, polycarbonates are suitable. Advantageous are those plastics which have the property of binding adsorptively as many reaction partners as possible such as e.g. polyvinylchloride, polymethylacrylate (Plexiglass). Polystyrene and copolymers of polystyrene (e.g. with acrylonitrile→Luran) are particularly preferably used for the process according to the present invention. When using polystyrene it is expedient to sterilize the carrier material by γ irradiation before coating. The carrier material is usually in the form of beads, microtitre plates, tubes, plates, foils, tissues/pads, microgels/latex.

The binding is carried out via a compound which has at least two functional groups which can be photoactivated and a hydrophobic moiety and, in addition, preferably an adequate solubility in water or buffer solution. In this process the hydrophobic moiety effects the adsorptive binding of this component to the carrier material, on the one hand, and to the immunologically active substance on the other hand. If it is then irradiated with light of a suitable wavelength and intensity, the highly reactive intermediate products (such as e.g. nitrenes, carbenes, radicals) which form react with the polymer molecules as well as with the protein molecules. In this way, an intermolecular cross-linkage of the protein with the plastic is formed. Functional groups are known which form highly reactive intermediate products under the influence of light of a particular wavelength. Azide, diazo and ketene residues are frequently used. The selection of the group which can be photoactivated also depends on the wavelength which is necessary for its activation. Since short-wave radiation can cause a photooxidative destruction of the proteins and, on the other hand, the use of radiation of particularly long wavelengths is disadvantageous, since then the sensitivity towards daylight is too high, the groups which can be photoactivated should be selected so that they are excited in a range from 250 to 500 nm, particularly preferably from 320 to 400 nm. The component (b) used according to the present invention can contain two or more groups which can be photoactivated which can be the same or different. A homo-bifunctional compound is preferably used as component (b). The part of the molecule linking the groups which can be photoactivated is at least partially hydrophobic. The hydrophobic moiety is thereby preferably so structured that the reagent has a hydrophobic interaction with the solid phase surface as well as with the substance to be immobilized which is as strong as possible. For this, the hydrophobic moiety has preferably a similar structure to the carrier material or the immunologically active substance. For example, when immobilizing proteins on polystyrene tubes or Luran tubes the hydrophobic moiety can contain condensed or multinuclear aromatic ring systems. A compound of the following general formula:

V—Hy—W is preferably used as component (b), in which V and W each denote a functional group which can be photoactivated and Hy denotes a hydrophobic group. In this connection a diphenyl, naphthyl or anthracyl residue in unsubstituted or substituted form is preferably used as the hydrophobic groups. In a particularly preferred embodiment of the invention a compound of the following formula:

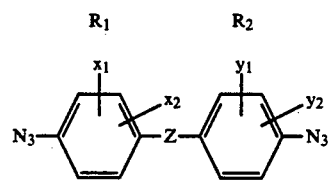

is used as component (b), in which $R_1$ and $R_2$ denote the hydrophobic moieties and $x_1$, $x_2$ and $y_1$, $y_2$ denote H, $NO_2$ or halogen, in each case independently from each other, and Z denotes a spacer group. The spacer group consists of the elements C, H, O, N and/or S and preferably has a chain length of 1 to 20 atoms. It is particularly preferred that Z represents the dithio group.

Immunologically active substance and the compound containing groups which can be photoactivated are used in such a ratio that the cross-linking and binding of the immunologically active substance is ensured. A molar excess of the compound which can be photoactivated from a factor of 1 to $10^6$, preferably of 3 to $3 \times 10^5$ particularly preferably of from 100 to 10000 has proven to be suitable for this.

After the coating, an irradiation is carried out to effect the desired cross-linking. Depending on the group used which can be photoactivated, the irradiation is carried out at a wavelength which generates highly reactive intermediate products but does not cause a photooxidative destruction of the proteins. Since tubes are very often used as carrier material, the wavelength should, in addition, preferably be in a range in which the irradiation can be carried out within the filled tube. The permeability of the tube to light is limiting for this.

The duration of irradiation depends on the reactivity and sensitivity to light of the groups which can be photoactivated and, as a rule, is between one second and one hour. The irradiation period is particularly preferably 30 to 60 minutes.

Known devices can in general be used for the irradiation. In this process, it should be taken care that a homogeneous irradiation of the tubes is ensured, since inhomogeneities lead to fluctuations in the adherence to the wall.

It is possible with the process according to the present invention to coat carrier material with an immunologically active substance without having to pretreat the substance or the surfaces. The process can be integrated in conventional production processes without large expenditure, since only one additional ingredient for the coating solution and an on-line irradiation of the carrier material are necessary. It can be applied universally and is suitable for immobilizing widely differing substances on many different available carrier materials. The process results in a significantly improved adhesion to the wall. The rates of detachment of the wall components during the function test and under stress by temperature and detergents are greatly reduced. The calibration curves, recoveries and precisions are unchanged compared to conventionally coated tubes.

The invention is elucidated by the following Figures and Examples:

FIGS. 1 to 5 show diagrams in which detachment data are plotted for coated tubes which were coated according to the process according to the present invention and for tubes which were adsorptively coated (denoted as "normal coated tubes" in the following):

EXAMPLE 1

Figure 2:
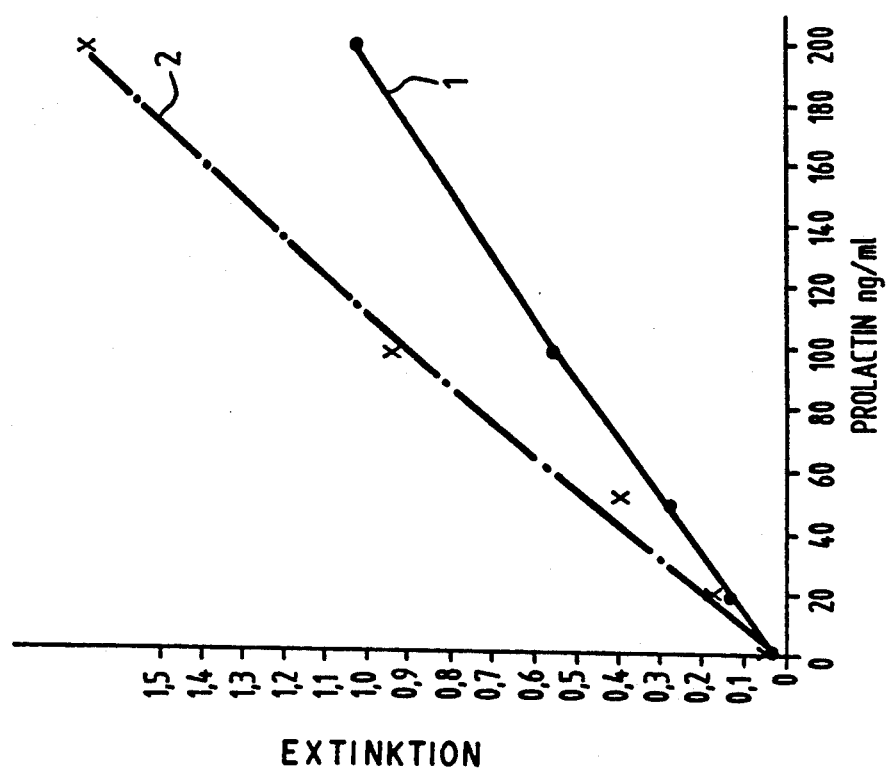
FIG. 2 Calibration curves for prolactin test at 37° C., $\lambda=405$ nm
curve 1: normal coated tubes
curve 2: photoimmobilized tubes
FIG. 3 Calibration curves for LH test at 20° C., $\lambda=405$ nm
curve 1: normal coated tubes (Luran)
curve 2: photoimmobilized tubes
FIG. 4 Calibration curves for T4 test at 20° C., $\lambda=405$ nm
curve 1: normal coated tubes (1 μg/ml)
curve 2: photoimmobilized tubes (1 μg/ml)
curve 3: photoimmobilized tubes (1 μg/ml)
FIG. 5 Calibration curves for T3 test at 30° C., $\lambda=405$ nm
curve 1: normal coated γ tubes
curve 2: normal coated polystyrene tubes
curve 3: photoimmobilized polystyrene tubes
curve 4: photoimmobilized γ tubes

Tubes were coated according to the process according to the present invention with different immunologically active substances. All antibodies, polyhaptens and binding proteins used, were radioactively labelled with $^{125}$I. The following were determined by means of radiometric measurements:
the amount of immunologically active substance bound to the solid phase (difference between the count rates of tubes filled with coating solution and tubes emptied out by aspiration after completion of the coating),
the detachment of the wall components during the function test (at different temperatures as well as under stress by detergents). For this, the coated tubes were measured in a γ-counter before and after carrying out the functional test or before and after incubation with buffers containing detergent (40 mmol/l sodium phosphate, pH 7.4). The displacement in percent was calculated from the differences between the measured count rates.

For further assessment, the coated tubes were used in function tests. The test criteria were calibration curves, precisions, recoveries and the tube stabilities. A normal i.e. adsorptively coated tube variant served as a reference in all measurements.

a) Adsorptive coating

The immunologically active substance (0.7 to 10 μg/ml) is incubated in 40 mmol/l phosphate buffer, pH 7.4 (or buffer I for the T4 test, cf. Example 4; buffer II for the TSH test, cf. Example 6; buffer III for streptavidin, cf. Example 7) for 24 hours at room temperature.

Subsequently, it is recoated as described under point b)2 of Example 1 and dried.

b) Photocoating (photoimmobilization)

The photocoating was carried out like the adsorptive coating with the following modifications:

1. The coating solution contained an addition of 1.5% ethanol and $1.10^{-5}$ mol/l 4,4-dithio-bisphenylazide. The concentration of the immunologically active substances (0.7 to 16 μg/ml) and the buffer concentration corresponded to the composition of the coating solution for the adsorptive coating. The modified coating solution was incubated in polystyrene tubes, γ irradiated polystyrene tubes (γ tubes) or Luran tubes for 20 to 24 hours at 20° C. in the dark.

2. After completion of the first incubation step the tubes which were still filled with the first coating solution, were irradiated for one hour under UV light at a wavelength of 366 nm. Subsequenly, the tubes are recoated (0.3% BSA solution with 0.9% sodium chloride and 2% saccharose, 30 min at 20° C.) and dried (24 hours and 40% relative humidity).

EXAMPLE 2

Figure 1:
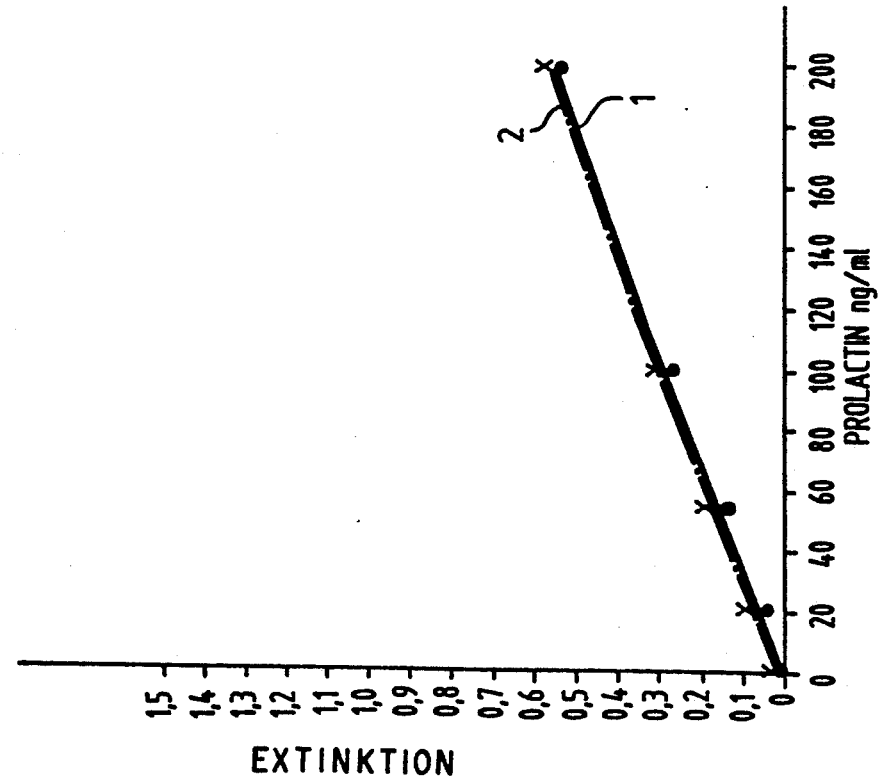
FIG. 1 Calibration curves for prolactin test at 20° C., $\lambda=405$ nm
curve 1: normal coated tubes
curve 2: photoimmobilized tubes.

Test tubes for a prolactin test were prepared according to the details of Example 1. The coating was carried out with 4 μg/ml antibody and $1.10^{-5}$ mmol/l 4,4'-dithio-bisphenylazide (DPA) in 40 mmol/l phosphate buffer, pH 7.4. The irradiation was carried out for 60 minutes at 366 nm. The results obtained with these tubes in comparison with tubes coated normally are shown in FIGS. 1 and 2 as well as in Tables 1 and 2. It turns out that also under stress by temperature and detergents markedly reduced rates of detachment are found with the photoimmobilized tubes with comparable calibration curves, precisions and recoveries. To carry out the function test 100 mU of a POD-labelled monoclonal antibody to prolactin in 1 ml buffer (40 mmol/l sodium dihydrogen phosphate, pH 7.4) were incubated together with 50 μl sample or standard for 30 minutes at 20° and 37° C. in the coated tubes. After washing twice with tap water, 1 ml ABTS ® substrate solution (1.9 mmol/l 2,2'-azino-di-[3-ethyl-benzthiazoline sulphonic acid (6)]-diammonium salt, 100 mmol/l phosphate-citrate buffer, pH 4.4, 3.2 mmol/l sodium perborate) was added and after 30 minutes the absorbance was measured at 405 nm.

TABLE 1

| | | normal coated tubes[1] | photoimmobilized tubes[1] |
|---|---|---|---|
| amount of bound protein (μg Ab/tube) | | 1.45 | 1.17 |
| coefficient of variation (n = 8) | | 1.9% | 2.5% |
| recovery of human sera (n = 5) | serum 1 | 100% | 102% |
| | serum 2 | 100% | 104% |
| | serum 3 | 100% | 100% |
| Ab detachment during function test | at 20° C. | 6.2% | 1.6% |
| | at 37° C. | 23.0% | 2.2% |
| Ab detachment under detergent stress | 1% Pluronic | 8.3% | 2.3% |
| | 1% SDS | 45.0% | 2.8% |
| | 0.5% Triton | 80.0% | 3.5% |

TABLE 1-continued

| | normal coated tubes[1] | photoimmobilized tubes[1] |
|---|---|---|
| (30 min, RT) | | | n: number of determinations
SDS: sodium dodecyl sulphate
RT: room temperature
Pluronic: Pluronic F68 (BASF), block polymers of ethylene oxide and propylene oxide
Triton: Triton ® X 100 (Rohm and Haas), ethoxylate of 4-(1,1,3,3-tetramethylbutyl)phenol
[1] made of Luran

TABLE 2

| | | normal coated tubes[2] | | photoimmobilized tubes[2] | |
|---|---|---|---|---|---|
| | | un-stressed 3 wk/ 4° C. (reference) | stressed 3 wk/ 37° C. | un-stressed 3 wk/ 4° C. (reference) | stressed 3 wk/ 37° C. |
| precision[1] (n = 3) | serum 1 x = 0.065 | 9.4% | 5.2% | 7.8% | 2.7% |
| | serum 2 x = 0.06 | 3.6% | 1.0% | 6.1% | 4.2% |
| | serum 3 x = 0.165 | 1.6% | 1.6% | 3.6% | 1.3% |
| recovery of human sera (n = 3) | serum 1 | 100% | 100% | 100% | 95% |
| | serum 2 | 100% | 105% | 100% | 92% |
| | serum 3 | 100% | 80% | 100% | 109% |
| recovery of standards n = 3 | std.* a | 100% | 112% | 100% | 107% |
| | std c | 100% | 92% | 100% | 95% |
| | std e | 100% | 93% | 100% | 95% |

*std = standard
x: mean absorbance,
[1] relates to absorbance values
[2] made of Luran

EXAMPLE 3

Figure 3:
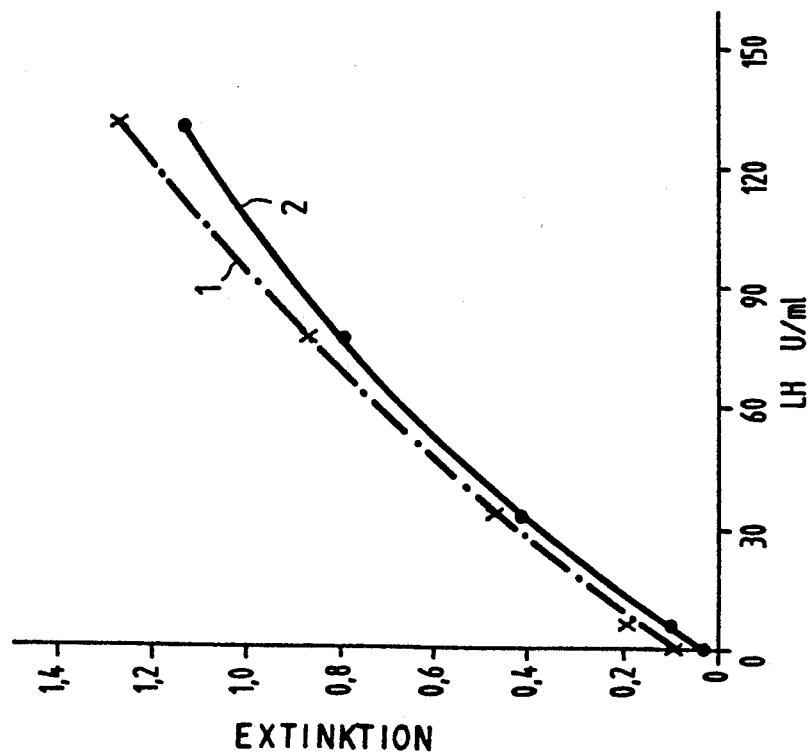

Tubes were coated for a LH test. The conditions were as described in Example 1. The coating was carried out with 1.5 μg/ml antibody in 40 mmol/l phosphate buffer, pH 7.2. The results with these tubes are shown in Table 3 as well as in FIG. 3. It turns out that the temperature and detergent stability are excellent with comparable calibration curves, precisions and recoveries. The amount of bound antibodies is in the same range as for the normal coated tubes.

In order to carry out the function test, 66 mU of a POD-labelled monoclonal antibody to LH in 1 ml buffer (40 mmol/l phosphate, pH 7.4) were incubated together with 100 μl sample or standard for 2 hours at 20° and 30° C. After washing three times with tap water, 1 ml ABTS ® substrate solution was added and the absorbance was measured after 30 min at 20° C. at 405 nm.

TABLE 3

| | | normal coated tubes | normal coated γ tubes | photoimmobilized γ tubes |
|---|---|---|---|---|
| amount of bound protein (μg Ab/tube) | | 1.05 | 1.30 | 1.12 |
| Ab detachment under detergent stress (30 min RT) | 1% Pluronic (n = 10) | 3.1% | 5.3% | 1.3% |
| | 0.5% Triton (n = 10) | 78.0% | 15.1% | 11.0% |
| Ab detachment during function test | buffer standards | 3.1% | 6.5% | 1.6% |
| | serum | 3.3% | 6.8% | 1.8% |

TABLE 3-continued

| | | normal coated tubes | normal coated γ tubes | photoimmobilized γ tubes |
|---|---|---|---|---|
| at 20° C. (n = 10) | standards human sera | 3.4% | 6.6% | 1.7% |
| Ab detachment during function test at 30° C. (n = 10) | buffer standards serum standards human sera | 9.6% 10.6% 9.7% | 11.0% 9.6% 12.4% | 3.2% 2.9% 2.9% |
| recovery of human sera (n = 3) | serum 1 | 100% | 66% | 92% |
| | serum 2 | 100% | 97% | 109% |
| | serum 3 | 100% | 92% | 95% |
| | serum 4 | 100% | 86% | 92% |
| | serum 5 | 100% | 96% | 98% |
| precision[1] (n = 3) | serum 1 | 14.9% | 7.4% | 12.9% |
| | serum 2 | 2.2% | 2.3% | 3.1% |
| | serum 3 | 5.2% | 7.4% | 5.5% |
| | serum 4 | 6.9% | 4.6% | 1.6% |
| | serum 5 | 4.3% | 4.0% | 3.2% |

[1] relates to absorbance values

EXAMPLE 4

Figure 4:
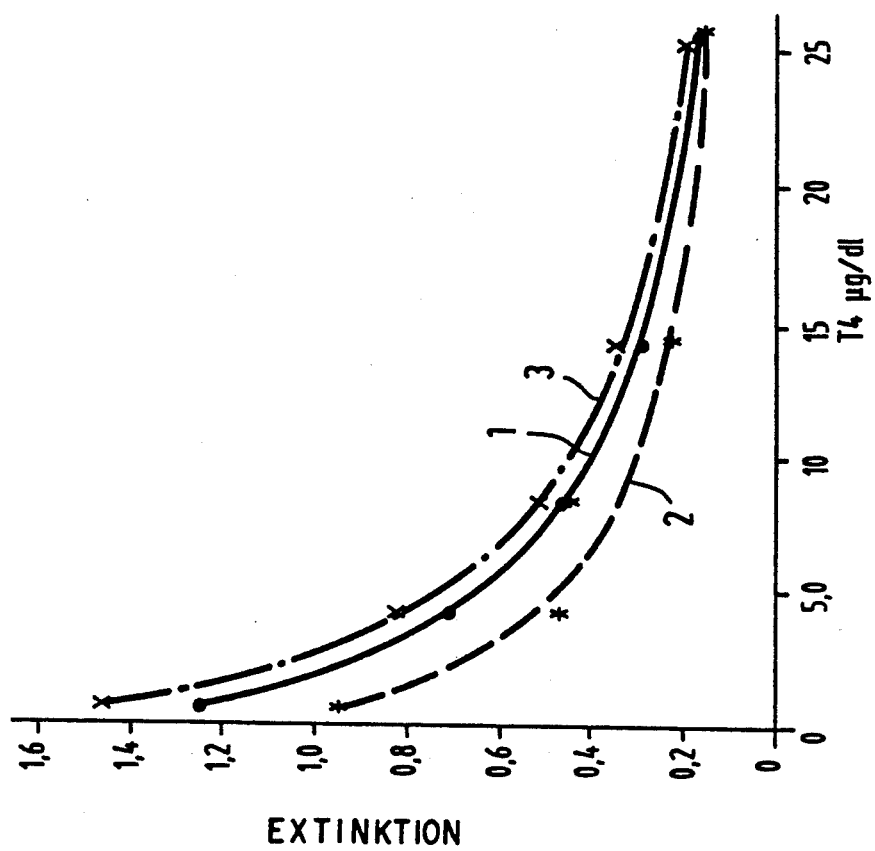

Tubes were coated for a T4 test. Two batches were produced in which a coating solution containing 1 μg/ml antibody and 2.5 μg/ml BSA phosphate buffer, pH 7.4 was used for the first batch and a coating solution containing 2 μg/ml antibody and 2.5 μg/ml BSA phosphate buffer, pH 7.4 was used for the second batch. The other coating conditions were as described in Example 1. The results are shown in Tables 4, 5 and 6 as well as in FIG. 4. Again, tubes were obtained with a very good tube stability and reduced rates of detachment in the function test and under stress by detergent. All in all, the precision was very good and the recovered values were in the range of the normal coated tubes.

TABLE 4

| | | normal coated tubes[2] | photoimmobilized tubes[2] |
|---|---|---|---|
| precision[1] (n = 30) | series 1 | 6.2% | 2.8% |
| | series 2 | 5.9% | 3.2% |
| | series 3 | 5.3% | 2.7% |
| recovery of human sera (n = 5) | serum 1 | 100% | 101% |
| | serum 2 | 100% | 108% |
| | serum 3 | 100% | 100% |
| Ab detachment during function test (n = 30) | series 1 | 9.1% | 3.2% |
| | series 2 | 8.9% | 3.2% |
| | series 3 | 8.1% | 2.8% |
| Ab detachment under detergent stress (30 min, RT) | 1% Pluronic | 11.0% | 2.8% |
| | 1% SDS | 44.0% | 12.0% |
| | 0.5% Triton | 86.0% | 16.0% |

[1] relates to absorbance values
[2] made of polystyrene

To carry out the function test, 15 mU of a T4-POD conjugate in 1 ml buffer I (120 mmol/l Na-barbiturate, 18.2 mmol/l phosphate, 0.04% ANS (8-anilino-1-naphthaline sulphonic acid), pH 8.6) were incubated in the tubes together with 20 μl sample or standard for 30 minutes at 20° C. After washing three times with tap water 1 ml ABTS ® substrate solution was added and the absorbance was measured after 30 min (20° C.) at 405 nm.

TABLE 5

|  | normal coated tubes[3] 1 μg Ab/ 2.5 μg BSA | photoimmo- bilized tubes[3] 1 g Ab/ 2.5 g BSA | photoimmo- bilized tubes[3] 2 g Ab/ 2.5 g BSA |
|---|---|---|---|
| amount of Ab bound (μg/tube) n = 15 | 0.425 (100%) | 0.352 (83%) | 0.70 (165%) |
| function signal stand. a (A) n = 15 | 1.253 (100%) | 0.927 (74%) | 1.466 (120%) |
| spec. reactivity ΔA/μg wall Ab n = 15 | 2.9 (100%) | 2.6 (89%) | 2.1 (72%) |
| Ab detachment in the function test[2] (n = 15) | 11.8% | 2.6% | 2.8% |
| Ab detachment under detergent stress[1] (n = 15) | 92.4% | 3.8% | 4.2% |

[1] 0.5% Triton 30 min, RT
[2] at 20° C.
[3] made of polystyrene

TABLE 6

|  |  | normal coated tubes[2] | | photoimmobilized tubes[2] | |
|---|---|---|---|---|---|
|  |  | un- stressed 3 wk/ 4° C. (refer- ence) | stress- ed 3 wk/ 37° C. | un- stressed 3 wk/ 4° C. (refer- ence) | stress- ed 3 wk/ 37° C. |
| precision (n = 3) based on absorbance | serum 1 x = 0.659 | 1.7% | 2.3% | 1.8% | 1.3% |
|  | serum 2 x = 0.653 | 1.7% | 0.8% | 2.3% | 2.8% |
|  | serum 3 x = 0.854 | 1.7% | 0.8% | 3.0% | 1.1% |
| recovery of human sera (n = 3) | serum 1 | 100% | 99% | 100% | 104% |
|  | serum 2 | 100% | 104% | 100% | 100% |
|  | serum 3 | 100% | 101% | 100% | 101% |
| recovery of standards[1] n = 3 | std.* a | 100% | 102% | 100% | 99% |
|  | std.* b | 100% | 102% | 100% | 103% |
|  | std.* d | 100% | 100% | 100% | 98% |

*std. = standard
[1] relates to absorbance values
[2] made of polystyrene

EXAMPLE 5

Figure 5:
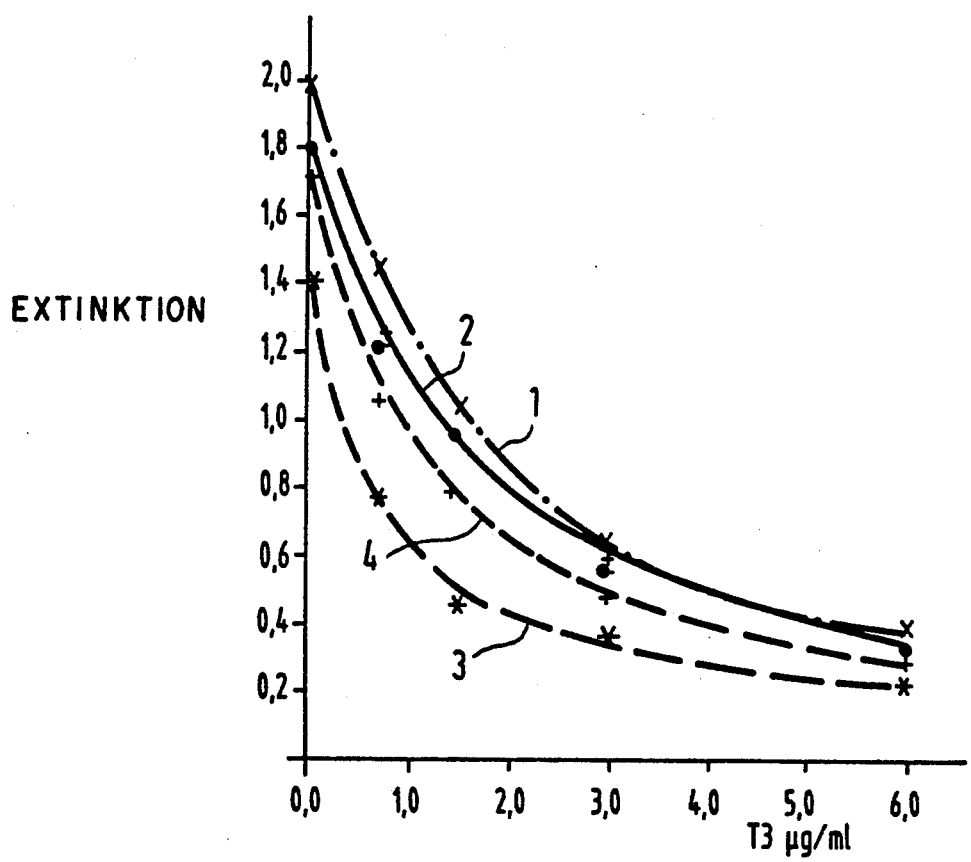

Tubes were coated for a T3 polyhapten test. For this, the tubes were incubated with a solution containing 0.75 μg/ml polyhapten (PH)/2 μg/ml R-IgG in 40 mmol/l phosphate buffer, pH 7.4. The other conditions were as described in Example 1. The results with these tubes are shown in the following Table 7 as well as in FIG. 5. The photoimmobilization also leads here to significantly reduced rates of detachment compared to normal coated tubes. The coating is stable to strong detergents and increased temperatures.

To carry out the function test, 80 mU of a POD-labelled antibody to T3 in 1 ml buffer II (120 mmol/l barbital buffer, 0.04% ANS) was incubated in the tubes together with 200 μl sample or standard for 30 min at 20° and 30° C. After washing twice with tap water 1 ml ABTS ® substrate solution was added and the absorbance was measured after 30 min at 20° C. at 405 nm.

TABLE 7

|  |  | normal coated PS tubes | normal coated γ tubes | photoimmo- bilized PS tubes | photoimmo- bilized γ tubes |
|---|---|---|---|---|---|
| amount of bound PH (μg/tube) n = 10 |  | 0.73 | 0.82 | 0.62 | 0.66 |
| function signal standard a (A) n = 5 | 20° C. | 1.24 | 1.16 | 0.7 | 0.9 |
|  | 30° C. | 1.83 | 1.98 | 1.34 | 1.72 |
| specific reactivity A/μg wall-PH n = 5 | 20° C. | 1.69 | 1.41 | 1.12 | 1.36 |
|  | 30° C. | 2.5 | 2.4 | 2.2 | 2.6 |
| PH detach- ment during function test n = 10 | 20° C. | 14.2% | 12.5% | 2.7% | 2.9% |
|  | 30° C. | 23.3% | 17.7% | 3.6% | 3.6% |
| PH detachment during detergent stress 0.5% Triton 20 min RT, n = 10 |  | 74.2% | 21.2% | 1.7% | 2.2% |

EXAMPLE 6

Tubes were coated for a TSH test. For this, the tubes were incubated with a coating solution containing 2 μg/ml antibody (Ab) to TSH under the conditions described in Example 1. An examination of the rates of detachment yielded the results shown in the following Table 8.

TABLE 8

Detachment of the wall components by detergents

|  |  | normal coated tubes | photoimmo- bilized tubes |
|---|---|---|---|
| amount of protein bound (μg/tube) n = 10 |  | 0.87 | 0.87 |
| Ab detachment during function test at RT (n = 5) | series 1 | 3.8% | 2.5% |
|  | series 2 | 3.2% | 2.9% |
|  | series 3 | 4.1% | 2.4% |
|  | series 4 | 4.3% | 2.9% |
|  | series 5 | 3.7% | 3.3% |
| Ab detachment under detergent stress (0.5% Triton, (30 min, RT) (n = 5) | series 1 | 75.4% | 1.9% |
|  | series 2 | 72.1% | 1.8% |
|  | series 3 | 74.3% | 1.8% |
|  | series 4 | 75.0% | 2.3% |
|  | series 5 | 79.7% | 2.0% |

EXAMPLE 7

Tubes coated with streptavidin and thermo-BSA-streptavidin (TBS) were produced according to EP-A 0 269 092. For the first batch, the tubes were incubated with a solution of 40 mmol/l phosphate buffer, pH 7.4 containing 4 μg/ml streptavidin under the conditions described in Example 1. In a second batch, tubes were incubated with coating solutions which contained 4 or 16 μg/ml TBS. The tubes were tested with regard to the wall adhesion or the biotin binding capacity (BiCa). To determine the relative biotin binding capacity, 18 ng biotin and 70 mU biotin-POD conjugate in 1.2 ml buffer III (40 mmol/l phosphate, pH 7.0, 0.5% Pluronic F68) were incubated in the tubes for 30 min. After washing (5 min) once with tap water 1 ml ABTS ® substrate solution was added and after 30 min the absorbance was measured at 405 nm. The results are shown in the following Tables 9 to 11. It can be seen that the photoimmobilization of streptavidin and TBS leads in part to a clear improvement in the wall adhesion.

TABLE 9

Detachment of the wall components in phosphate buffer with 2% Pluronic (incubation time 30 minutes at 20 and 30° C.)

| tube variant | % detachment 20° C. | % detachment 30° C. |
|---|---|---|
| a) Streptavidin tubes | | |
| Luran tubes | 17.8 | 28.0 |
| Luran tubes, photoimmobilized | 3.1 | 5.7 |
| | | n = 5 |
| b) Thermo-BSA-streptavidin tubes | | |
| Luran tubes | 3.1 | 11.6 |
| Luran tubes, photoimmobilized | 0.8 | 1.7 |

TABLE 10

| tube variant | % detachment 1% Pluronic F68 (30 min, RT) | % detachment 0.5% Triton (30 min, RT) |
|---|---|---|
| a) Streptavidin tubes | | |
| Luran tubes | 13.9 | 42 |
| Luran tubes, photoimmobilized | 3.3 | 9.4 |
| b) Thermo-BSA-streptavidin tubes | | |
| Luran tubes | 2.1 | 8.0 |
| Luran tubes, photoimmobilized | 0.9 | 0.8 |

TABLE 11

| | normal coated tubes | | | | photoimmobilized tubes | | | |
|---|---|---|---|---|---|---|---|---|
| | coating concentration 4 µg/ml | | coating concentration 16 µg/ml | | coating concentration 4 µg/ml | | coating concentration 16 µg/ml | |
| | Lu | γ | Lu | γ | Lu | γ | Lu | γ |
| amount of bound TBS µg/tube | 3.6 | 3.78 | 5.05 | 5.26 | 3.05 | 3.06 | 4.57 | 4.73 |
| relative BiCa (absorbances) | 0.68 | 0.7 | 1.16 | 1.16 | 0.25 | 0.21 | 0.39 | 0.28 |
| TBS detachment during BiCa test | 0.8% | 1.8% | 2.0% | 1.7% | 1.6% | 1.3% | 2.1% | 1.9% |
| TBS detachment 1% Pluronic 30 min, RT | 3.3% | 2.9% | 1.6% | 0.4% | 1.0% | 0.6% | 1.2% | 1.2% |
| TBS detachment 0.5% Triton 30 min, RT | 18.6% | 1.3% | 21.5% | 1.5% | 1.1% | 0.6% | 1.2% | 1.2% | n = 5

We claim:

1. Process for the production of a solid phase matrix coated with an immunologically active substance, comprising the steps of:
a) adsorptively coating a carrier material selected from the group consisting of polyamide, polyacrylamide, polyester, polycarbonate, polyvinylchloride, polymethylacrylate, polystyrene and copolymers of polystyrene, with a mixture of (a) an immunologically active substance and (b) a linking or bridging compound which contains at least two functional groups which can be photoactivated and at least one moiety which interacts adsorptively to link the immunologically active substance to the carrier material in the absence of radiation capable of photoactivating said at least two functional groups, thus producing a coated carrier material, and
b) subsequently irradiating the coated carrier material to intermolecularly cross-link the immunologically active substance and the carrier material via the linking or bridging.

2. Process as claimed in claim 1, wherein the immunologically active substance is selected from the group consisting of antibodies, antigens or binding proteins.

3. Process as claimed in claims 1 or 2, wherein the immunologically active substance and the linking or bridging compound which can be photoactivated are used in a molar ratio of 1:1 to $1:1 \times 10^6$.

4. Process as claimed in claims 1 or 2, wherein anti-T4 antibodies, anti-prolactin antibodies, anti-LH antibodies, anti-TSH antibodies, T3-polyhapten, streptavidin, thermo-BSA-streptavidin and/or polystreptavidin are used as the immunologically active substance.

5. Process as claimed in claims 1 or 2, wherein a homo-bifunctional compound is used as the linking or bridging compound.

6. Process as claimed in claims 1 or 2 wherein a compound of the general formula is used as the linking or bridging compound in which V and W are the same or different and each denote a functional group which can be photoactivated and Hy denotes a hydrophobic group.

7. Process as claimed in claims 1 or 2, wherein a compound of the following formula:

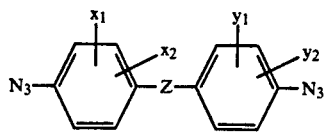

is used as the linking or bridging compound in which $x_1$, $x_2$ and $y_1$, $y_2$ denote H, $NO_2$ or a halogen, in each case independently from each other, and Z denotes a spacer group.

8. Process as claimed in claims 1 or 2, wherein the irradiation is carried out at a wavelength of 250 to 500 nm.

9. Process as claimed in claims 1 or 2, wherein the irradiation is carried out at a wavelength of 320 to 400 nm.

10. Process as claimed in claims 1 or 2, wherein the coated solid phase matrix is irradiated for 0.5 to 1 hour.

11. The process of claim 1 wherein the carrier material is selected from the group consisting of polyvinyl chloride, polymethylacrylate, polystyrene, and polystyrene copolymers.

12. The process of claim 1, wherein the carrier material is polystyrene.

13. The process of claim 1, wherein the carrier material is polystyrene-acrylonitrile copolymer.

* * * * *